United States Patent [19]
Tseng

[11] Patent Number: 6,152,142
[45] Date of Patent: Nov. 28, 2000

[54] GRAFTS MADE FROM AMNIOTIC MEMBRANE; METHODS OF SEPARATING, PRESERVING, AND USING SUCH GRAFTS IN SURGERIES

[76] Inventor: Scheffer C. G. Tseng, 10000 SW. 63rd Pl., Pinecrest, Fla. 33156

[21] Appl. No.: 09/027,109

[22] Filed: Feb. 20, 1998

Related U.S. Application Data

[60] Provisional application No. 60/039,486, Feb. 28, 1997.

[51] Int. Cl.$^7$ ...................................................... A61B 19/00
[52] U.S. Cl. ................................................ 128/898; 623/4
[58] Field of Search ................................. 128/898; 623/4

[56] References Cited

PUBLICATIONS

Badawy, et al. "Evaluation of Tissue Healing and Adhesion Formation After an Intraabdominal Amniotic Membrane Graft in the Rat," 34 *J. Reproductive Med.* 198 (1989).

Yokomori, et al., "Advantages and Pitfalls of Amnion Inversion Repair for the Treatment of Large Unruptured Omphalocele: Results of 22 Cases," 23 *Journal of Pediatric Surgery* 882 (1992).

Sorsby, et al., "Further Experience with Amniotic Membrane Grafts in Caustic Burns of the Eye," 31 *Br. J. Opthamology* 409–18 (1947).

Sorsby and Symons, "Amniotic Membrane Grafts in Caustic Burns of the Eye (Burns of the Second Degree)," 30 *Br. J. Opthamology* 337–345 (1946).

*Primary Examiner*—V. Milliw
*Assistant Examiner*—Kelly O'Hara
*Attorney, Agent, or Firm*—Robert M. Schwartz; Gerald R. Hibnick

[57] ABSTRACT

A method for making, storing and using a surgical graft from human amniotic membrane; the resulting graft; and the storage solution. The amniotic membrane is obtained from human placenta, from which the chorion has been separated. Sheets of the amniotic membrane are cut to size and mounted on filter paper. The cells of the amniotic membrane are killed, preferably while being frozen and thawed in the storage solution. The storage solution comprises a culture medium and a hyperosmotic agent, wherein the hydration of the amniotic membrane is maintained. The membrane can be impregnated with therapeutic agents, prior to storage, for use in post surgical healing or other therapies.

12 Claims, No Drawings

GRAFTS MADE FROM AMNIOTIC MEMBRANE; METHODS OF SEPARATING, PRESERVING, AND USING SUCH GRAFTS IN SURGERIES

CROSS-REFERENCE TO RELATED APPLICATIONS

This application claims the benefit of U.S. Provisional Application No. 60/039,486, filed Feb. 28, 1997.

BACKGROUND OF THE INVENTION

1. Field of Invention

This invention relates to amniotic membrane grafts especially usable in the repair of injured eyes. This invention also encompasses: a method for separating and preserving amniotic membrane for a graft; the graft that is created by such method; and methods of repairing eyes and other organs while using these grafts.

2. The Prior Art

Terminology:

An amniotic membrane has two major components: the basement membrane and stroma. The side of the amniotic membrane dominated by the basement membrane is referred to as the "basement membrane side". The side of the amniotic membrane dominated by the stroma is referred to as the "stroma side". An autograft is a tissue transplant from the same recipient. When used in subcutaneous tunnels, autografts of the amnion become a permanent structure. In contrast, allografts are replaced by hyaline-like material. An allograft is a tissue transplant to a recipient from a donor of another individual of the same species.

Previous Clinical Applications

The fetal membrane including amnion (amniotic membrane) and chorion has been used in surgeries documented as early as 1910 and has been reviewed by Trelford and Trelford-Sauder in 1979. See Trelford and Trelford-Sauder, *The Amnion in Surgery, Past and Present*, 134 AM J. OBSTET. GYNECOL 833 (1979). In the beginning, the fetal membrane was used by Davis in 1910 on burned and ulcerated skins with additional coverage of warm paraffin and dressing. In 1940, De Rötth used fetal membrane for ophthalmic reconstruction of symblepharon, and noted a success in one out of six cases. See De Rötth, *Plastic Repair of Conjunctival Defects with Fetal Membranes*, 23 ARCHIVES OF OPTHAMOLOGY 522 (1940). In 1952, Douglas thought chorion might be more useful for skin use. Massee and colleagues in 1962 used the fetal membrane in dogs to treat pelvic basins after total exenteration; however, the human trials proved disappointing.

The isolated amnion alone was first used by Brindeau in 1935 and Burger in 1937 as a graft in forming artificial vaginas. Between 1941 and 1948, Kubanyi used "live" amnion in patients with burns, traumatic skin wounds, and enterocutaneous fistula secondary to surgery for lysis of adhesions. The isolated amnion, with preservation in a technique termed "amnioplastin", was first reported by Chao and associates in 1940. Chao used amnioplastin for continual dural repair, peripheral nerve injuries, conjunctival graft and flexor and tendon repair. In the Russian literature, this technique was also used for fresh trauma by Pikin in 1942.

Although all reports were enthusiastic, mention of "amnioplastin" disappeared from the literature with no real explanation. No critical reports regarding isolated, non-living amnion with preservation were found for a thirty-year period. Furthermore, if there were failures of treatment during this time, they were not reported. This gap in research ended in 1972 with the research of Trelford and associates, cited above. Trelford, using isolated amnion with an early form of preparation, showed that the orientation with stromal side down provided more consistent "take." Robson and colleagues noted in 1972 that, when used in partial-thickness skin wounds, no "take" occurs, and the amnion peels off. In 1973 and later, Trelford and associates reported its use as a dressing on full-thickness skin wounds, to replace pelvic peritoneum, and to cover exposed deep surfaces in pedicle graft procedures, to treat non healing skin wounds in diabetic patients, as a graft over the surgical defect of total glossectomy, as a biological dressing in omphalocele, and in the prevention of meningocerebral adhesions following head injury.

Previous Methods of Preparation and Preservation:

All of the above-mentioned applications appeared to have used live tissues or tissue removed and preserved "lively" in a special solution before use. For example, de Rötth put the fetal membrane, amnion and chorion together without separation, in "tepid Locke solution", and one to fifteen hours after cesarean section the tissue was implanted to patients. Reports which appeared after 1980 refer to live amniotic membranes having been used (See 34 J. REPRODUCTIVE MED. 198 (1989) and 27 J. PEDIATRIC SURGERY 882 (1992)). For "amnioplastin", Chao and associates isolated the amnion, placed it in 70% alcohol, and then dried it in an oven prior to use. Robson and associates rinsed the membrane in a 0.025% NaOH solution and showed that it remained sterile up to six weeks when stored in saline containing penicillin at 4° C. Trelford and associates found that amniotic membranes stored at 4° C. in 0.5N saline to which polymyxin, ampicillin, gentamicin, and amphotericin B was added were sterile at the end of four hours and remained so for at least 48 hours.

SUMMARY OF THE INVENTION

Human amniotic membrane, obtained and preserved in a new way is made into a graft which is effective in: promoting healing of persistent corneal epithelial defects with ulceration; reduction of inflamation, angiogenesis and scarring; restoration of the epithelal phenotype; numerous further uses in ocular surface reconstruction; and as a substrate alternative to conjunctival autograft during the "bare sclera" removal of pterygia. In addition, when combined with limbal allografts, amniotic membrane transplantation is useful for ocular surface reconstruction in patients with advanced ocular cicatricial pemphigoid, Stevens-Johnson syndrome, chemical and thermal burns, aniridia, atopic keratitis and idiopathic limbal stem cell deficiency. After the placenta is obtained and cleaned, the amnion is separated from the chorion by blunt dissection, flattened onto filter paper with the epithelium surface facing away from the paper, and cut into small sheets. These sheets are stored in a media composed, for example, in Dulbecco's Modified Eagle Medium and glycerol at the ratio of 1:1 (v/v), and frozen at −80° C. until just prior to use as a graft. When thawed to room temperature the day of use, the cells of the graft membrane have been killed, probably by ice crystals from the surrounding storage medium. The side of the membrane adherent to the filter paper is opposed to the surgical site.

OBJECTS OF THE INVENTION

It is an object of this invention to prepare grafts made from amniotic membrane.

It is another object of this invention to prepare grafts made from amniotic membrane that can be stored for long periods of time.

It is another object to this invention to prepare grafts that have been treated so that the grafts contain agents that can be delivered to the recipient when attached to the recipient.

It is another object of this invention to provide an improved substrate alternative to conjunctival autograft during the "bare sclera" removal of pterygia.

It is another object of the invention to provide an improved substrate alternative to conjunctival flaps to promote healing of corneal epithelial defects with ulceration.

It is another object of this invention to provide an improved method for conjunctival surface reconstruction for symbelpharon lysis.

It is another object of this invention to provide an improved method for surgical removal of tumors, lesions, or scar tissue from the conjunctival or corneal surface.

It is another object of this invention to reduce the corneal haze induced by excimer laser photerefractive/therapeutic keratectomy.

It is another object of this invention to promote successful glaucoma surgeries by correcting bleb leakage.

It is another object of this invention to prevent recurrence of band keratopathy.

Other objects of the invention and advantages over the prior art, as well as differences from the prior art, will become fully appreciated from the following discussion of: Embryogenesis and Histology; Components; Applications in Basic Research; and the Description of the Preferred Embodiments, along with description of numerous proposed uses of the resulting, improved graft.

Embryogenesis and Histology

Early in the process of blastocyst implantation, a space develops between the embryonic mass and adjacent trophoblasts. The amniotic epithelium is derived from fetal ectoderm (the embryonic disc). In addition to the epithelial cells, a layer of fibroblast-like cells might also be derived from the embryo, but this is not certain. The important "missing" elements of human amnion are smooth muscle cells, nerves, lymphatics, and, most important, blood vessels. The human amnion likely develops about the 7th and 8th day of development of the normal blastocyst. Amnion fuses with chorion during the 10th and 12th weeks of pregnancy, when the amniotic cavity expands. The amnion remains avascular till term. This is the reason why separation between amnion and chorion is possible via the interface, i.e., the intermediate zone. The normal amnion is 0.2 to 0.5 mm in thickness.

Histologically, the amnion is comprised of five layers. The inner surface consists of a simple cuboidal epithelium, which lies on the basement membrane. The avascular stromal contains fetal mesenchyme and includes the compact layer, fibroblastic layer and spongy layer. Four distinct anatomic portions of the amnion exist. First, the reflected amnion is that portion that is contiguous with the chorion laeve. Second, the placenta amnion overlies the fetal surface of the placenta, which is directly contiguous with the adventitial surface of the chorionic vessels. Third, the amnion also covers the umbilical cord, that is contiguous with Wharton jelly. Wharton Jelly is the extracellular matrix through which the umbilical vessels traverse. Fourth, in diamnioin-dichorionic twin pregnancy, the amnion are "fused", which in the former is contiguous with fused chorion laeve and in the latter amnion is fused with amnion.

Components:

Different tissues of the body have different components of collagen and glycosaminoglycans (hereinafter "GAGs").

The amniotic stroma has been shown to contains collagens I and III and fibronectin, and has a perilaminal distribution of collagen types V and VII. The basal lamina of the amnion contains a network of type IV collagen fibrils, laminin, and heparin sulfate proteoglycan. The collagenous fibers of the amnion are closely distributed with no ground substances, forming a thick collagenous layer. In human and monkey placenta, hyaluronic acid (hereinafter "HA") is thought to be the only GAGs found, but this finding is not shown in the amnion yet. This compositional feature is in part responsible for the tensile strength noted during pregnancy.

The basement membrane side of the amniotic membrane can be used to support epithelial growth to maintain epithelial polarity. When growing human fibroblasts or A431 epidermal carcinoma cells, the stromal side of the amniotic membrane is found to be comparable to isolated collagen, but greater than a plain plastic surface in culturing cell growth. When sandwiched in the Boyden chamber, this membrane can be used for studies of polymorphous nuclear cells emigration (hereinafter "PMN emigration") in the process of leukodiapedisis, vascular endothelial invasion, and tumor cell metastasis, through the basement membrane. Although the amnion is not innervated, avian amnion express at least eleven different types of receptors for neurotransmitters, including: acetylcholine, norepinephrine, histamine, 5-hydroxytryptamine, VIP, urotensin II, neurotensin, and somatostatin-28.

Applications in Basic Research:

Taking advantage of its basement membrane content, human amnion can be used as a substrate to culture peripheral and central nervous system neurons and to promote axonal regeneration when implanted in the central nervous system. This effect appears not dependent on the live cells and is mediated by the amniotic matrix, which promotes the host regenerative power, and can be further enhanced when added with nerve growth factor (hereinafter "NGF") in regeneration of a severed peripheral nerve.

DESCRIPTION OF THE PREFERRED EMBODIMENTS

Method for Selection, Preparation and Preservation of the Graft:

To prepare and preserve grafts from human amniotic membrane, the following method should be used.

First, the placenta is taken as soon as possible after the delivery. Preferably, the placenta is taken immediately following the elective cesarean section (C/S) delivery of a normal healthy baby.

To avoid any potential blood-transmittable diseases, the pregnant female is prescreened for HIV-1, HIV-2, HTLV-1, hepatitis B and C viruses and syphilis, using conventional serological tests. Only those placentas of which the maternal bloods reveal negative serological results are used for this method to produce the amniotic graft.

Human placenta that meet the above selection criteria is transferred to the laboratory in a sterile plastic bag stored in an ice bucket. The following procedures are performed under sterile conditions, as routinely used for tissue cultures.

1. Under a lamellar-flow hood, the placenta is rinsed several times with balanced salt saline to remove excessive blood clots. Balanced saline solution is available, for example under the trademark BSS® from Alcon Inc., 6201 South Freeway, Fort Worth, Tex., 76101. The rinse also should contain antibiotics to aid in the cleaning and preserving. An example of an effective antibiotic formulation contains 50 $\mu$g/ml penicillin, 50 $\mu$g/ml streptomycin, 100

μg/ml neomycin, and 2.5 μg/ml amphotericin B. In addition, the membrane can be treated so that it contains other substances that would be transferred to the recipient once the graft is placed. Examples of substance which can be impregnated into the graft membrane are: therapeutics, hormones, polypeptides; to aid healing of the surgical area or other therapies.

2. With two sets of forceps, the placenta's amniotic membrane is separated easily from the remaining chorion by blunt dissections, while immersed in the above antibiotics-containing balanced saline solution.

3. The separated amniotic membrane, as a sheet, then is mounted/apposed onto a substrate, for example, a sterile nitrocellulose filter, so that the epithelial surface is kept facing up when flattened. Thus, the stromal/fibroblistic layer lies on the filter. The basement membrane lies above the stromal layer, and the epithelial lies above the basement membrane. The filter should be inert with respect to the amniotic membrane and the next discussed storage medium. The filter should not contain bleach or chlorine and should be stable when in the storage medium, especially when subject to freezing and thawing therein. One source of such a filter is Millipore, Inc. and is sold as product number 162-0180. Other useful substrates are nitro cellulose membranes 162-0115, supported nitro cellulose membrane 162-0090 and blot absorbent filter paper 162-0118, all from Biorad.

Sheets of amniotic membranes that have been adhered/mounted onto the nitrocellulose filter are cut to different sizes, for example, 2.5–3.0 cm.×2.0–2.5 cm. and 1.2–1.5 cm.×1.75–2.0 cm. and are stored in a culture medium at temperatures below freezing. It is important to appreciate that the freezing of the grafts (the cut up and filter mounted sheets of amniotic membrane) and their subsequent thawing, soon prior to the use, results in the killing of the cells of the membrane, probably by ice crystals formed in the membrane from the liquid in the culture medium. By killing the cells, the resulting graft thereby is not rejected after surgery. However, the integrity of the extracellular matrix is not altered despite the freezing and thawing. Although the cells could be killed by other, conventional, means, the use of freezing-thawing does not introduce agents or conditions which might adversely affect the stored membrane or the completed graft, to cause it not to "take" or be rejected, impair the healing of the eye, etc. As previously noted, the prior art used media to keep the cells vital (alive) and did not recognize the great advantage of killing the cells. While any temperature below freezing should work, a temperature of −80° C. has been used typically to store the grafts. Furthermore, this method of preservation is effective with respect to sterility and efficacy for long-term storage beyond one year, even when the thus stored and frozen cut sheets of membrane are shipped long distances in dry ice.

An example of an effective medium is comprised by 50% Dubecco Modified Eagle's Medium (hereinafter "DMEM medium") (from GIBCO) and 50% glycerol (V/V). A range of 30% to 50% glycerol is usable. The function of the glycerol is to maintain the hydration state of the amniotic membrane; too little or too much hydration is detrimental, 60% to 90% hydration is effective for the intended purpose. The glycerol acts as a high oncotic or hyperosmotic agent; another term for which is a plasma expander. Examples of other usable hyperosmotic agents are: dextran, albumin, and mannitol. The general purpose of the storage medium, such as DMEM, is to provide nutrients to and maintain electrolyte balance for the amniotic membrane. Other examples of a suitable storage medium are: Liebowitz's medium, MEM, and NCTC, all manufactured by Life Technologies.

If the sheets of amniotic membrane, on the filter paper, are to be used "near term", within twenty-four hours of harvesting, then the use of a storage medium is not essential; however, the cells do have to be killed, as previously stated.

Graft prepared according to the previously-stated method:

A graft comprising amnion, from human placenta, which has had the chorion removed, that is prepared and preserved according to the previously-stated method. This graft has been rinsed with balanced salt solution and antibiotics. The graft can contain therapeutic substances that have been absorbed into it. The graft is mounted onto filter paper, having suitable characteristics, as previously stated. The graft is stored in a composition of culture medium and a high oncotic agent at freezing temperatures. Prior to use, the graft is thawed.

Method of using prepared amniotic membrane as a surgical graft:

In eyes with persistent epithelial defect and ulceration, after retrobulbar anesthetic injection, the base of the ulcer is debrided with surgical sponges (an example of a suitable surgical sponge is sold under the trademark MICRO-SPONGE® from Alcon Surgical, Inc., 6201 South Freeway, Fort Worth, Tex. 76134-2099) and 0.12 forceps, and the poorly adherent epithelium adjacent to the edge of the ulcer also is removed to the area where the epithelium becomes quite adherent. The amniotic membrane, which recently was removed from the storage medium and thawed to room temperature, is peeled off from the nitrocellulose filter paper, transferred to the recipient eye, with the stromal surface facing the eye and fitted to cover the defect by trimming off the excess edges of the membrane/graft sheet. In other instances, the opposite side can be used. This fashioned membrane then is secured to the edge of the defect by interrupted 10-0 nylon sutures, and in some cases by a running 10-0 nylon suture. After the knots are buried, the corneal surface becomes smoothed as a result of the well-approximated amniotic membrane filling in the ulcer bed. Except for deep ulcers, one layer of membrane generally is sufficient. But it is also feasible to use two or more layers. A bandage contact lens is applied together with a topical ophthalmic antibiotic ointment comprising neomycin, polymyxin b sulfate and dexamethasone. An example of such a suitable ophthalmic antibiotic ointment is sold under the trademark MAXITROL® from Alcon Laboratories, Inc., 6201 South Freeway, Fort Worth, Tex. 76134.

The inventions herein are more effective than that of De Rötth in conjunctival surface reconstruction for symblepharon lysis. In addition, the invention can be used to reconstruct the conjunctival surface which is damaged during surgical removal of tumor, lesion, or scar tissue. Impression cytology can prove that the reconstructed conjunctiva regain normal epithelial phenotype with goblet cells of which the number is greater than the normal control. Goblet cells secret mucin and are shaped like a goblet. A membrane produced through the invented method, when used as a patch, can reduce corneal haze, a form of scarring, induced by excimer laser photo refractive keratectomy and therapeutic keratectomy, a procedure presently used in patients to correct myopia and astigmatism, and to remove the diseased part of corneas, respectively. Also this method and product can be used by itself or in conjunction with stem cell transplantate to reconstruct surfaces damaged by various causes leading to nimbal stem cell deficiency.

This amniotic graft can be used for promoting successful glaucoma surgeries by correcting bleb leakage. The surgical use of amniotic grafts made according to the inventions herein can prevent recurrence of band keratopathy, prevent adhesion during muscle surgeries, and help orbit reconstruction in oculoplastic surgeries. Band keratopathy is the deposition of calcium on the corneal surface.

In addition to the mentioned ophthalmic uses, it is envisioned that the amniotic membrane of this invention also can be used: as a graft or dressing to cover burned or surgical skin wounds; to prevent adhesion in all intra peritoneal surgeries or other reconstruction on the serosal surfaces covering the abdomen, chest cavity and pericardium;

to reconstruct all mocosal surfaces lining the oral and nasal cavities, respiratory tracts, gastrointestinal tracts, and urogenital tracts; as a substrate to support dural repair in brain surgeries; as a substrate to promote nerve regeneration in the central and peripheral nervous systems; and to reconstruct soft tissues to prevent adhesion in joint or tendon repairs.

It is believed that surgeons, scientists and researchers will benefit from the information provided in the following papers:

1. Kim J C, Tseng S C G. Transplantation of preserved human amniotic membrane for surface reconstruction in severely damaged rabbit corneas. Cornea. 1995;14:473–84.

2. Tsubota K, Satake Y, Ohyama M, et al. Surgical reconstruction of the ocular surface in advanced ocular cicatricial pemphigoid and Stevens-Johnson syndrome. Am J Ophthalmol. 1996;122:38–52.

3. Lee S. Tseng S C G. Amniotic membrane transplantation for persistent epithelial defects with ulceration. Amn J Ophthalmol. 1997;123:303–312.

4. Prabhasawat P, Barton K, Burkett G, Tseng S C G. Comparison of conjunctival autografts, amniotic membrane grafts and primary closure for pterygium excision. Ophthalmology. 1997;104:974–985.

5. Tseng S C G, Prabhasawat P, Lee S. Amniotic membrane transplantation for conjunctival surface reconstruction. Am J Ophthalmol. 1997; December issue, 124:765–774.

6. Prabhasawat P, Tseng S C G. Impression cytology study of epithelial phenotype of ocular surface reconstructed by preserved human amniotic membrane. Arch Ophthalmol. 1997; November issue, 115:1360–1367.

7. Barton K, Budenz D L, Khaw P T, Tseng S C G. Amniotic membrane transplantation in glaucoma surgery. Invest Ophthalmol Vis Sci 1997; 38:S473.

8. Wang M, Gray T, Prabhasawat P, Ma X, Ding F-y, Hernandez E, Sanabria O, Culbertson W, Hanna K, Forster R K, Tseng S C G. Corneal haze is reduced by amniotic membrane matrix in excimer laser photoablation in rabbits. Invest Ophthalmol Vis Sci 1997; 38:S405.

9. Tseng S C G, Prabhasawat P, Barton K, Gray T B, Meller D. Amniotic membrane transplantation with or without limbal transplantation for corneal surface reconstruction in patients with limbal stem cell deficiency. Arch Ophthalmol, in press 1998 (April).

While there has been described preferred embodiments of this invention's methods and products, and there has been mentioned modifications thereto; other changes, variations and modifications can be made within the scope of the appended claims, without departing from the spirit and scope of this invention.

What I claim is:

1. A method for obtaining human amniotic membrane and preparing it to be used as a surgical graft, comprising the steps of:

obtaining human placenta and cleaning it;

separating said placenta's amniotic membrane from its chorion, said amniotic membrane having cells and an extracellular matrix;

mounting said amniotic membrane onto a substrate, with the epithelial surface of said membrane facing away from said substrate; and killing the cells of said membrane prior to using said membrane as a surgical graft and maintaining the integrity of said extracellular matrix.

2. A method according to claim 1, in which;

said step of killing said cells is accomplished by freezing said amniotic membrane in liquid; and thawing said membrane prior to using it as a graft.

3. A method according to claim 2, in which;

said freezing step is accomplished after said mounting step;

and said thawing step is just prior to use of said membrane as a graft.

4. A method according to claim 2, in which;

said liquid is a culture medium.

5. A method according to claim 4, in which;

said liquid is a hyperosmotic reagent.

6. A method according to claim 2, in which;

said liquid is DMEM medium and glycerol.

7. A method according to claim 1, in which;

said substrate is a sterile nitrocellulose filter further including the steps of;

separating said amniotic membrane from said filter; and securing said membrane to a surgical site as a graft, with the stromal layer of said membrane facing said site.

8. A method according to claim 7, in which;

said surgical site is a human eye.

9. A method according to claim 8, and employing said graft with associated medical/surgical steps for any one of:

an autograft during the bare sclera removal of pterygium;

promoting healing of corneal epithelial defects with ulceration;

conjunctive surfacere construction for symbelpharom lysis;

reducing scaring;

maintaining a normal epithelial phenotype;

removing tumors, lesions, scar tissue from conjunctival or corneal surfaces;

reducing corneal haze induced by excimer lasers; promoting correct bleb leakage;

preventing recurrence of band keratopathy; and helping orbit reconstruction in oculoplastic surgeries;

reconstructing corneal surface damaged by libal stem cell deficiency as a result of various causes.

10. A method according to claim 1, and employing said amniotic membrane graft with associated medical/surgical steps for any one of:

a dressing over skin wounds;

preventing adhesion in surgeries;

reconstructing mocosal surfaces;

supporting, as a substrate, dural repair;

promoting nerve repair as a substrate;

reconstructing soft tissues; and reducing scaring.

11. A method according to claim 1, and providing said amniotic membrane with at least one of a therapeutic, a hormone, a polypeptide, for becoming part of said graft.

12. A method according to claim 1, in which;

said obtaining is from a human female during a cesarean section delivery.

* * * * *